United States Patent
Hennig (10) Patent No.: US 8,456,636 B2
(45) Date of Patent: Jun. 4, 2013

(54) DEVICE FOR DETECTING SIGNS OF BACTERIAL INFECTION OF THE TEETH

(75) Inventor: Thomas Hennig, Langenfeld (DE)

(73) Assignee: Ferton Holding, S.A., Delemont (CH)

( * ) Notice: Subject to any disclaimer, the term of this patent is extended or adjusted under 35 U.S.C. 154(b) by 256 days.

(21) Appl. No.: 12/680,936

(22) PCT Filed: Oct. 1, 2008

(86) PCT No.: PCT/EP2008/008329
§ 371 (c)(1),
(2), (4) Date: May 13, 2010

(87) PCT Pub. No.: WO2009/046922
PCT Pub. Date: Apr. 16, 2009

(65) Prior Publication Data
US 2010/0216087 A1   Aug. 26, 2010

(30) Foreign Application Priority Data
Oct. 1, 2007   (DE) .......................... 10 2007 047 067

(51) Int. Cl.
*G01N 21/55*   (2006.01)
(52) U.S. Cl.
USPC ........................................................ 356/445

(58) Field of Classification Search
USPC ............................. 356/71, 432–444, 445–448
See application file for complete search history.

(56) References Cited

U.S. PATENT DOCUMENTS

| 4,718,406 A | * | 1/1988 | Bregman et al. ............... 600/130 |
| 5,570,182 A |   | 10/1996 | Howard et al. |
| 2007/0188738 A1 | * | 8/2007 | Jung et al. ....................... 356/73 |

FOREIGN PATENT DOCUMENTS

| DE | 4200741 A1 | 7/1993 |
| DE | 10 2004 024494 A1 | 12/2005 |
| DE | 19541686 B4 | 8/2009 |
| WO | 2007/147262 A | 12/2007 |

OTHER PUBLICATIONS

International Search Report dated Mar. 9, 2009 to corresponding international patent application No. PCT/EP2008/008329 filed Oct. 1, 2008, 3 pages.

* cited by examiner

*Primary Examiner* — Michael P Stafira
(74) *Attorney, Agent, or Firm* — Maier & Maier PLLC (57) ABSTRACT

The invention relates to a device for detecting signs of bacterial infection of teeth, comprising a light source, a receiving unit, an evaluation unit, coupled to the receiving unit, at least one emission fiber, coupled to the light source, and at least one detection fiber, coupled to the receiving unit. The invention is characterized in that both the emission and detection fiber have an acceptance angle of more than 35°.

19 Claims, 5 Drawing Sheets

DEVICE FOR DETECTING SIGNS OF BACTERIAL INFECTION OF THE TEETH

RELATED APPLICATIONS

This application claims priority, under 35 U.S.C. §119, to German patent application No.: 10 2007 047 067.5, filed on Oct. 1, 2007, the disclosure of which is incorporated by reference herein in its entirety.

The invention refers to a device for detecting signs of bacterial infection of teeth according to the preamble of claim 1.

Such a device is known e.g. from DE-A-42 00 741. Said document discloses a device for the detection of caries on teeth, comprising an illumination unit for emitting radiation in the wavelength range of 360 to 580 nm onto a tooth. A filter will allow the passage of fluorescent radiation in a wavelength range larger than 620 nm returned by the tooth. The radiation allowed to pass through will be evaluated for detection of caries.

Known from DE-A-195 41 686 is a further device for measurement of fluorescent radiation wherein a light source will emit excitation radiation in a wavelength range between 600 and 670 nm onto a tooth under examination. The fluorescent radiation excited on the tooth will be detected and evaluated in a wavelength range between 670 and 800 nm.

In previously known devices, the substantially axial emission of the radiation from the respective light conductor cable turned out to be disadvantageous because, due to the substantially axial emission of the radiation, a sufficient illumination of linear portions of narrow cavities, e.g. gingival pockets, is not possible. For this reason, previously known devices are provided with additional optical elements at the radiation exit end of the light conductor cables, which elements cause a not inconsiderable expenditure in manufacture and will considerably enlarge the total diameters of the light conductor cables.

It is an object of the invention to provide a device of the kind initially described, wherein bacterially infected sites in narrow cavities, such as e.g. in gingival pockets, can be detected better even without using additional optical elements.

The object is achieved with the features of claim 1.

The invention advantageously provides that in a device of the kind initially described comprising a light source, a receiving unit, an evaluation unit coupled to the receiving unit, at least one emission fiber coupled to the light source, and at least one detection fiber coupled to the receiving unit. The invention is characterized in that both the emission fiber and the detection fiber have an acceptance angle of more than 35°.

Alternatively, the acceptance angle of the emission and detection fibers can be larger than 40°, preferably larger than 45°.

The emission and detection fibers can be guided within a light conductor cable.

Said acceptance angle larger than 35° corresponds to an opening angle of at least 70°. The advantage of an acceptance angle larger than 35° resides in that the bundle of emission and detection fibers of the present invention will be capable to illuminate also linear cavities without the need to use additional optical elements. In the inventive emission and detection fibers having an acceptance angle larger than 35°, the maximal intensity which is obtained laterally of the light exit surface, is considerably higher than in usual quartz-glass light conductors which are no wide-angle light conductors. Moreover, the present device according to the invention is easy to handle.

The emission and detection fibers can be provided with a single or multiple coating.

The numerical aperture of the light source can be greater than or equal to the numerical aperture of the at least one emission fiber.

The light source used can be an LED chip.

In contrast to laser devices, LEDs radiate light in a wide opening angle. Normal LEDs mounted on a substrate will thus radiate circularly in all directions.

The transmission of light in a light conductor is performed substantially without a change of the opening angle, which is to say that, when exiting from the light conductor, the light will have the same opening angle as upon entrance.

Thus, in order to be able to realize light with a wide opening angle on the exit end of the emission fibers, it is provided, according to a further embodiment that the incoupling is performed without using optical lenses and that a distance of less than 0.3 mm and preferably of 0 mm exists between the LED chip and the proximal end face of the emission fiber.

By the elimination of optical lenses, significantly larger opening angles can be realized.

Between the LED chip and the proximal end face of the at least one emission fiber, a medium can be arranged which has a refractive index between that of the emission fiber and that of the surface of the LED chip. In this manner, the reflection losses at the transitions will be minimized. Preferably, the medium introduced into the intermediate space is optically transparent.

According to a further embodiment, the proximal end face of the emission fibers adjacent to the light-emitting surface of the LED chip is smaller than the light-emitting surface of the LED chip and is completely covered by the light-emitting surface of the LED chip.

According to a further embodiment, the LED chip is operative to emit light in the UV range and/or the adjacent visible range, preferably violet light in the wavelength range from 390 to 420 nm. The radiation in this wavelength range can very efficiently detect the optical differences between healthy and bacterially infected teeth.

The distal end face of the bundle of emission and detection fibers can be coupled to the proximal end face of at least one light-conducting element, wherein the light-conducting element can be made of sapphire or a mineral material or plastic and have an acceptance angle larger than 35°. The acceptance angle can also be larger than 40°, preferably larger than 45°. The light-conducting element may be uncoated, have a single or multiple coating.

The at least one light-conducting element can be guided within an inspection probe comprising a shaft and a coupling portion. Said inspection probe can be connected to a handle portion. The shaft can be rigid or flexible. The shaft may also be curved or be flexible.

The light-conducting element can also be rigid or flexible.

The light-conducting element can be operative for conducting the excitation radiation emitted by the light source via the emission fibers to the tooth, and also for conducting the fluorescent radiation emitted by the tooth.

The light-conducting element can consist of a single light conductor or of a plurality of light conductors, i.e. of a light conductor bundle.

The total diameter of the light-conducting element can be larger than or equal to the total diameter of emission and detection fibers.

The distal end face of the bundle of emission and detection fibers and the proximal end face of the light-conducting element can be pressed against each other by means of a spring force.

The proximal end face of the light-conducting elements and the distal end face of the bundle of emission and detection fibers can have spherical surfaces, respectively.

By way of alternative to using the light-conducting element, the emission and detection fibers can be guided directly, i.e. without interposition of a light-conducting element, to the tooth. Also the emission and detection fibers can be guided at the distal end within an inspection probe comprising a shaft and a coupling portion.

The two above described embodiments with inspection probe will allow for easier handling because, due to the curved shaft, the bundle of emission and detection fibers and respectively the light-conducting element can be easily introduced e.g. into gingival pockets.

The emission and detection fibers can terminate with the distal end of the shaft or project relative to the shaft by maximally about 5 cm.

According to a further embodiment, it is provided that the proximal end of the inspection probe is connectable to a handle portion, wherein the emission and detection fibers can be guided within said handle portion. In the embodiment in which an additional light-conducting element is coupled to the bundle of emission and detection fibers, the connection site can be situated within the handle portion between the bundle of emission and detection fibers and the light-conducting element.

This has the advantage that the device can be handled in a more convenient manner because said handle portion allows for a better guidance of the bundle of emission and detection fibers or the light-conducting element.

Said light source can be arranged within the handle portion.

According to a further embodiment, it is provided that the length of the emission fiber or the total length of the emission fiber and the light-conducting element is less than 60 cm, preferably less than 10 cm.

These embodiments have the advantage that the emitted light does not have to cover long distances from the light source to the tooth, which is relevant since, in wide-angle light-conductors, the intensity of the radiation will decrease with increasing length of the transmission distance.

In a development it is provided that the receiving unit comprises a semiconductor arrangement in which three sensors are arranged within an area. The three sensors capture the fluorescent radiation excited at the tooth via the at least one emission fiber and returned by the tooth, the radiation being captured in three mutually separated wavelength ranges. The at least one detection fiber can be arranged centrically above the semiconductor sensor arrangement at a defined distance from the surface of the semiconductor sensor arrangement.

The light cone exiting from the proximal end of the detection fiber will illuminate the sensor surface of the semiconductor sensor arrangement without interposition of optical lenses.

Present prior art has the disadvantage that an examination in a region where different dental filling materials are present, erroneous results can be obtained. However, it is just at the interface between dental material and filling material that information about whether a tooth is bacterially infected or not is of particular interest.

The invention has the advantage that the sensors used will capture the fluorescent radiation excited on the tooth in three mutually separated wavelength ranges and that an evaluation unit will evaluate the radiation. Because of the various kinds of tissues present in the mouth and the different filling materials, a diagnosis based on an analysis of three spectral ranges will be significantly more precise and reliable.

In comparison to the previous state of the art, this has the advantage that the returned radiation does not have to be guided via separate light conductor cables to different optical receivers and does not have to be distributed among the optical receivers via mirrors or other optical elements. Further, no optical elements, especially lenses, are required to illuminate the sensor surface.

With the aid of a light-conductor support, the detection fiber is held centrically over the semiconductor sensor arrangement and at a predetermined distance from the surface of the semiconductor sensor arrangement, said light-conductor support being fastened to the casing of the semiconductor sensor arrangement.

Said three sensors can be sensors for radiations lying in the wavelength ranges of the basic colors red, green and blue, respectively. The three sensors can also be sensors for radiations lying in other wavelength ranges, i.e. in the wavelength radiations of mixed colors.

The sensors can be arranged within a circular surface, and the respective basic color can have assigned thereto a circular surface segment of 120°.

This embodiment has the advantage that the returned radiation will be equally distributed onto the sensors because the detection fiber is positioned centrically to the semiconductor sensor arrangement.

Said three sensors are not restricted to being arranged within a circle but can also be arranged in any desired configuration relative to each other.

The sensor for radiation in the wavelength range of the basic color red has the highest sensitivity and is responsive up to at least 750 nm.

This has the advantage that the red fluorescence, which is weak relative to the green fluorescence, will be intensified so that an electrical crosstalk will be prevented.

An optical prefilter for suppression of excitation radiation can be arranged between the at least one detection fiber and the semiconductor sensor arrangement and be fixed on the semiconductor sensor arrangement with the aid of an optically transparent casting compound.

The thickness of the optical prefilter can be less than 2 mm. The prefilter can be a dielectric filter.

Further, the semiconductor sensor arrangement can be arranged on a conductor plate which is shielded against electromagnetic radiation with the aid of an electrically conductive layer of copper.

As an alternative, use can be made of any desired layer which is effective for shielding against electromagnetic radiation.

Between the receiving unit and the evaluation unit, three separate amplifiers can be arranged for amplification of the respective signals of the sensors.

The evaluation unit can have stored therein different sets of data in the form of three-dimensional measurement values, wherein the evaluation unit will compare the measured measurement values to said sets of data and will output a result relating to the bacterial infection of examined tooth portions.

Further, the fluorescence signals of the light-conducting element can be detectable by the three sensors of the semiconductor sensor arrangement, By comparing the measuring signals generated by the three sensors with the reference data sets of different materials as stored in the evaluation unit, also the material of the at least one light-conducting element is detectable, wherein the evaluation unit can indicate which material the light-conducting element is made of.

The information on the material that the light-conducting element is made of, can be supplied to software means. Said software means determines, inter alia, the sensitivity with which the measurement values are to be evaluated. The supply of the information to said software means has the advantage that the sensitivity of the measurement can be adapted to the material of the light-conducting element. This is to say that the sensitivity with which the measurement values are evaluated can be adapted to the purpose of the application.

Embodiments of the invention will be explained in greater detail hereunder with reference to the drawings.

The drawings show the following schematic representations:

FIG. 1 shows a principal block diagram of a device according to the invention. Excitation radiation from a light source 18 will be coupled into a bundle of emission fibers 14 and be transported by these to a tooth 1. Said emission fibers 14 are guided together with detection fibers 16 to a light-conductor cable 12. On its distal end, said light-conductor cable 12 is coupled to a handle portion 10. The emission fibers 14 and the detection fibers 16 are guided in said handle portion 10 and in an inspection probe 2. Said inspection probe 2 comprises a coupling portion 6 and a shaft 4. The proximal end of said coupling portion 6 can be connected to the distal end of handle portion 10. Said shaft 4 is preferably made of metal or plastic. The fluorescent radiation excited by the excitation radiation on the tooth 1 will be transported via detection fibers 16 to a receiving unit 20. On their distal end 8, the emission and detection fibers 14,16 preferably terminate together with the distal end of shaft 4. At the most, the emission and detection fibers 14,16 project by about 5 cm relative to the second shaft.

Figure 1:
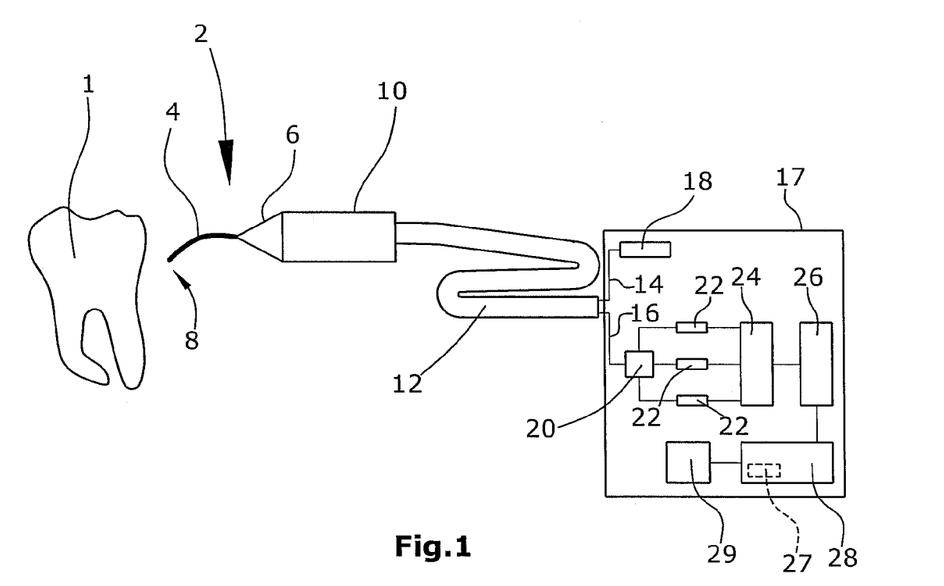
FIG. 1 is a principal block diagram of the device according to the invention.

In said receiving unit 20, the fluorescent radiation will be detected in three mutually separated wavelength ranges and be converted into three electric signals. These will be transmitted, via separate preamplifiers 22, to a lock-in amplifier 24. By means of a subtractor 26, connected downstream of said lock-in amplifier 24, background signals can be subtracted. Background signals are caused by reflection of the excitation radiation at the distal end 8 of the emission and detection fibers 14,16 as well as by a slight inherent fluorescence of the light-conducting fibers and the adhesives used. The amount of the signal is directly proportionate to the excitation radiation. If the excitation radiation is kept constant, a constant offset signal will be obtained. This background signal will be measured during the switch-on routine of the measurement device and will be eliminated in said subtractor 26 prior to evaluation. Within the evaluation unit 28, there is arranged a memory 27 having stored therein the three-dimensional measurement values of healthy tooth material, diseased tooth material and synthetic filling material. The term "three-dimensional" is to be understood in the sense that, for each measurement value, the radiation intensity will be measured in three spectral ranges, e.g. in the spectral ranges of the basic colors red, green, blue. The currently measured three-dimensional measurement value will be compared to the stored comparative measurement values, and the distances to the closest comparative measurement value of healthy tooth material and/or synthetic filling material and diseased tooth material will be determined. The ratio of the distance between the currently measured measurement value and the closest comparative measurement value of healthy tooth material and synthetic filling material and the distance between the currently measured measurement value and the closest comparative measurement value of diseased tooth material will be indicated in the form of values on a display unit 29. The user will know that, if this value is smaller than a certain value, the examined tooth region is free of bacterial remnants.

Figure 2A:
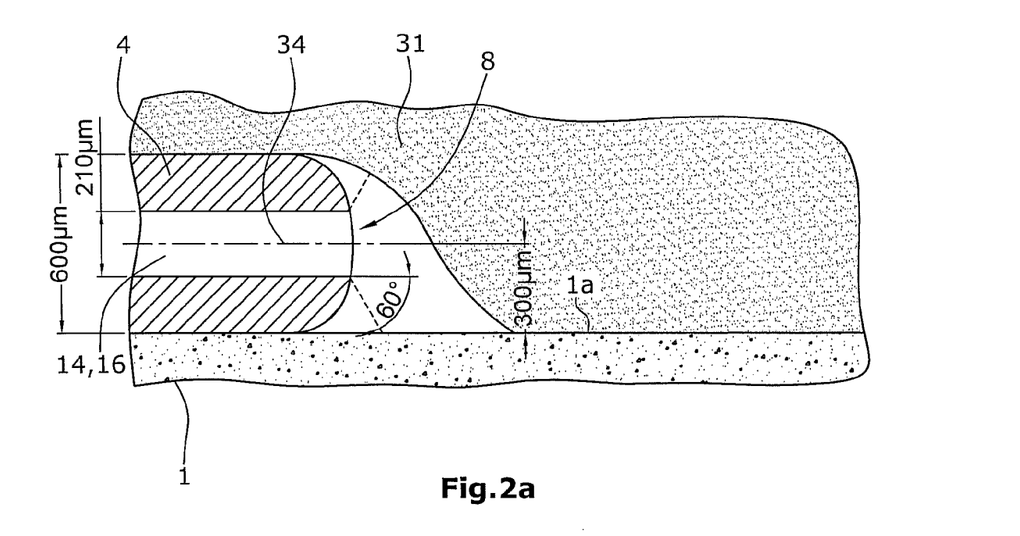
FIG. 2a is a view of a wide-angle light conductor whose axis is oriented parallel to a tooth surface.
Figure 2B:
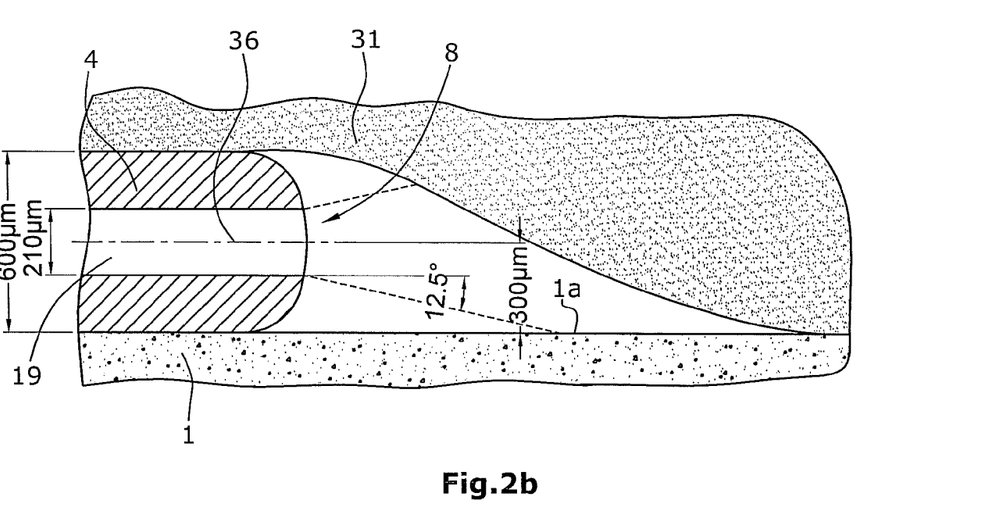
FIG. 2b is a view of a quartz-glass light conductor which is not a wide-angle light conductor and whose axis is oriented parallel to the tooth surface.

FIGS. 2a and 2b show a first light conductor bundle 14, 16 and a second light conductor bundle 19, each comprising emission and detection fibers. Both the first light conductor bundle 14, 16 and the second light conductor bundle 19 are guided in a shaft 4. As can be seen in FIGS. 2a and 2b, the respective shaft 4 is positioned between the gum 31 and the tooth 1. In both Figures the two light cones shed by the first and the second light conductor 14, 16, 19 are plotted in dotted lines. FIG. 2a illustrates a light cone of the light conductor bundle 14, 16 representing a bundle of wide-angle light conductors. For comparison, FIG. 2b illustrates the light cone of a bundle of conventional quartz-glass light conductors which are no wide-angle light conductors. The center axes 34, 36 of the first and second light conductor bundles 14, 16, 19 are spaced by e.g. 300 μm in parallel to the tooth surface is which is substantially planar in this portion. In the embodiments illustrated, the diameters of the first and second light conductor bundles 14, 16, 19 are 210 μm each. The wide-angle light conductors emit light under an opening angle of 120°, corresponding to an acceptance angle of 60°. The conventional quartz-glass light conductors, which are no wide-angle light conductors, have an opening angle of e.g. 25°. In FIG. 2a, the gum abuts closely on the tooth. Nevertheless, since wide-angle light conductors have been used, it is still possible to examine the surface of the tooth. Using conventional quartz-glass light conductors having a typical opening angle of 25°, an illumination in a narrow gingival pocket would not be possible. Quartz-glass light conductors which are no wide-angle light conductors can only be used (see FIG. 2b) if the space between the tooth and the gum, that is the gingival pocket, is significantly larger than in FIG. 2a.

Preferably, glass light conductors having an acceptance angle of more than 35°, preferably more than 40°, are used as wide-angle light conductors. However, it is also possible to use wide-angle light conductors of plastic material, preferably polystyrene.

Figure 3:
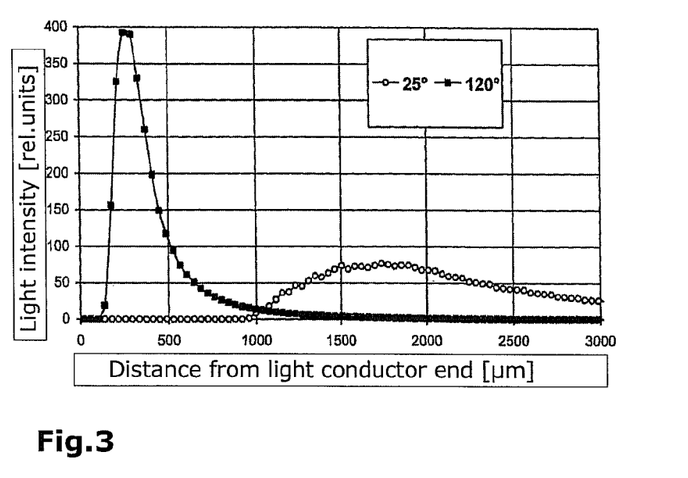
FIG. 3 is a diagram of the light distribution on the plane surface of FIG. 2a and FIG. 2b.

FIG. 3 shows the light intensity distributions in a test arrangement on a plane surface (instead of the tooth surface 1a and the gum) under geometrical conditions corresponding to those of FIGS. 2a and 2b. The light conductors and the plane surface are at the same distances and under the same relative orientations as the light conductor bundle 14, 16 and the tooth surface 1a in FIGS. 2a and 2b, the difference being that the light conductors in the test arrangement do not illuminate a gingival pocket so that the light beams are not limited by the gum. The light beams can impinge on the plane surface without being hindered. The light exit surface, i.e. the free end of the light conductors, is located at the value 0 on the abscissa. The white dots represent the light intensity distribution for common quartz-glass light conductors having an opening angle of 25°, and the black squares represent the light intensity distribution for wide-angle light conductors having an opening angle of 120°. One can see clear differences between the two curves. An opening angle of only 25° will lead to a flat shape of the curve. The maximal light intensity obtained on the plane surface 30 has a distance substantially between 1.5 mm and 2 mm from the light exit surface of the light conductor end. In case of an opening angle of 120°, the maximal light intensity obtained on the plane surface has a distance of only about 0.3 mm from the light exit end. In the case of the wide-angle light conductor as used in the device according to the invention, the maximum intensity achieved on the plane surface is more than five times higher than the maximum intensity of a usual quartz glass light conductor which is not a wide-angle light conductor. This has the consequence that distinctly more-accurate measurement values can be obtained because the signal/noise ratio is considerably better. In a wide-angle light conductor, the examined surface portion is significantly shorter and better illuminated than in usual quartz glass light conductors which are no wide-angle light conductors, as evident from FIGS. 2a and 2b. The ratio between the bacterially infected surface and the examined surface portion has a direct influence on the measurement values, which is to say that, if the bacterially infected surface is small in comparison to the examined surface portion, the contamination can be read from the measurement values only with difficulties, which is due to the small percentage of the contaminated surface relative to the total surface portion under examination. Thus, as evident from FIG. 3, when using normal quartz-glass light conductors with large examined surfaces and weak illumination, smaller contaminated areas can easily happen to be overlooked. In wide-angle light conductors with a relatively short surface portion and intense illumination, the ratio between the contaminated surface and the examined surface portion with regard to the percentage is more favorable so that contaminated surfaces can be detected more distinctly and accurately. For this reason, the examined tooth portions, particularly in narrow cavities, can be examined with greater accuracy when using the wide-angle light conductor of the invention.

Figure 4:
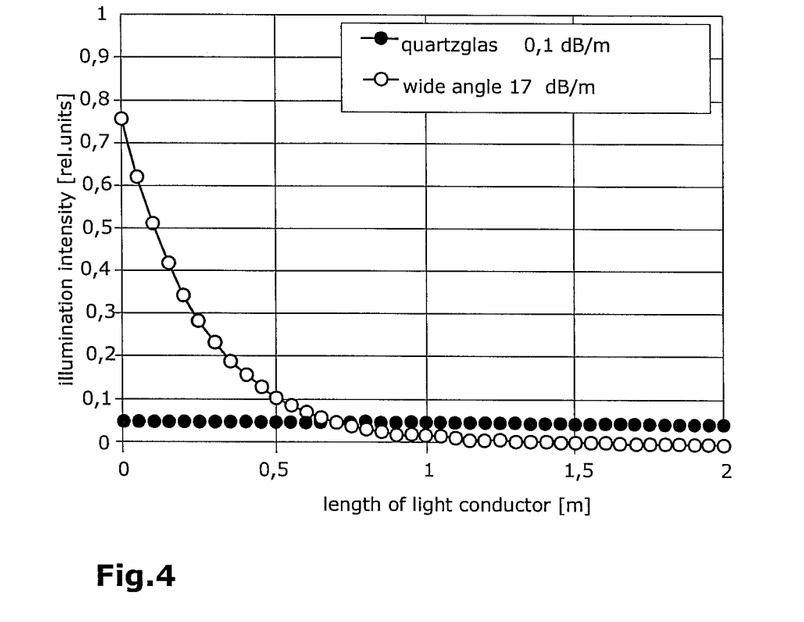
FIG. 4 is a diagram representing the relationship between the damping of the illumination strength and the length of the light conductor.

FIG. 4 shows the illumination strength at the end of various light conductors relative to the illumination strength at the entrance to the light conductors in dependence on the length of the light conductors. The relative illumination strength was calculated according to the following formula:

$$B = NA^2 * 10^{-((a*L)/10)}$$

B: illumination strength
NA: numerical aperture
a: damping of the light-conductor in dB/m
L: length of the light-conductor in m The open circles relate to a wide-angle light conductor with an opening angle of 120°. In the range of 400 nm, this wide-angle light conductor has a damping of about 17 dB/m. The black dots relate to a quartz-glass light conductor with an opening angle of 25°. In the range of 400 nm, this quartz-glass light conductor has a damping of about 0.1 dB/m.

Figure 9:
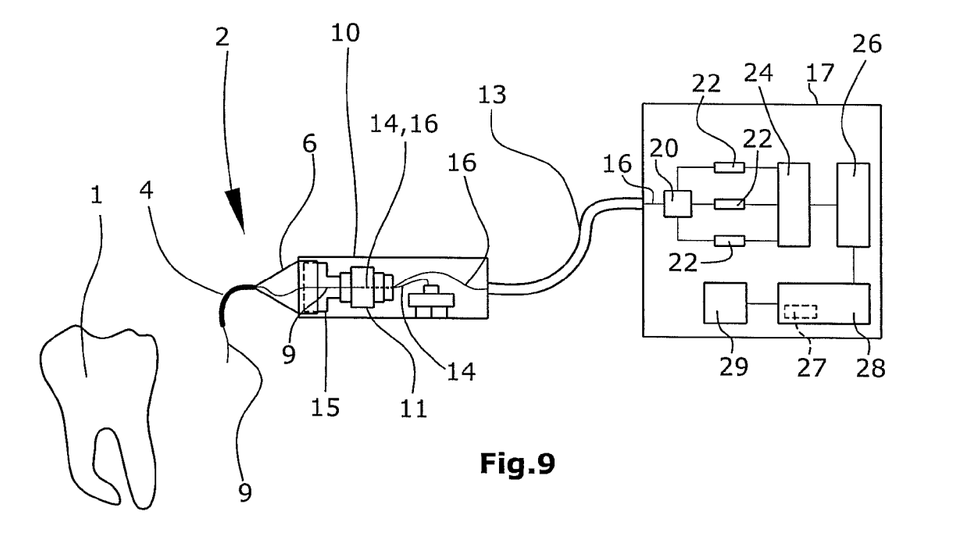
FIG. 9 is a view of a device with a light-conducting element.

From FIG. 9, it is evident that, especially in wide-angle light conductors, long light-conducting fibers will cause a weakening of the light available on the exit surface, which is the case particularly in the short-wave spectral range around 390-420 nm that is of interest for fluorescence excitation. To avoid this damping effect, the light-conducting fibers, in case that a wide-angle light conductor is used, should have a length of less than 60 cm, preferably less than 10 cm. It is obvious from FIG. 4 that with wide-angle light conductors shorter than 10 cm, it is possible to accomplish an illumination strength at the light exit end that is about 10 times higher than with the usual quartz-glass light conductors which are no wide-angle light conductors.

Considering FIG. 3 and FIG. 4, one may summarize that a light intensity that is about 50 times higher can be achieved on an examined surface of a substance that is parallel to the axis of the wide-angle light conductor. It is obvious from FIG. 3 that, using a wide-angle light conductor, a light intensity can be achieved on an examined surface of a substance that is parallel to the axis of the wide-angle light conductor that is about 5 times higher than with light conductors that are not wide-angle light conductors. It can be taken from FIG. 4 that it is possible to achieve an illumination intensity, or in other words light intensity, at the light exit surface that is about 10 times higher. As a consequence, if a wide-angle light conductor shorter than 10 cm is used, it is possible to achieve a light intensity on an examined surface of a substance that is parallel to the axis of the wide-angle light conductor that is 50 times higher.

Figure 5:
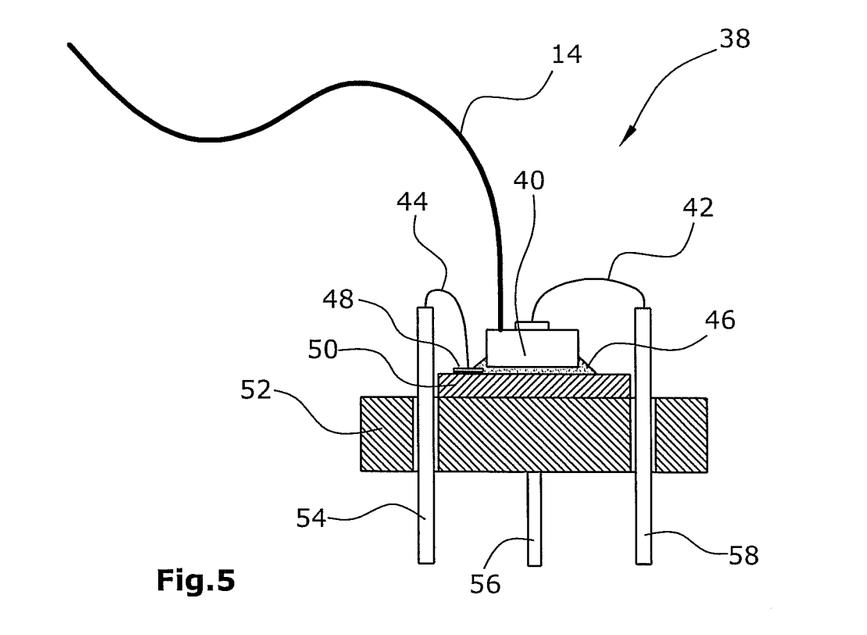
FIG. 5 is a view wherein the light source is an LED chip.

FIG. 5 shows an LED chip 40 connected opposite to the emission fibers 14. This is to say that, between the surface of the LED chip and the proximal end face of the emission fibers 14, there remains a distance being less than 0.3 mm and preferably being 0 mm. Between the LED chip surface and the emission fibers 14, a preferably transparent medium, e.g. synthetic resin, not shown, can be arranged which has a refractive index between that of the emission fibers 14 and that of the LED chip surface. With the aid of said transparent medium, e.g. a curable plastic, the emission fibers are mechanically tightly fastened to LED chip 40 and optically coupled thereto. By use of an electrically conductive adhesive 46, LED chip 40 is mounted to a monitor diode chip 50 and electrically contacted thereto, Said monitor diode chip 50 delivers a measurement value which is proportionate to the optical output line of LED chip 40. From an electric contact site 48, a bond wire 44 is connected to an electric connection pin 54 guided in an insulating manner in the socket 52. Said monitor diode 50 comprises a second electric contact in the form of a housing pin 56 which is guided to the outside. Also LED chip 40 comprises a second electric connection. This connection is realized via a bond wire 42 which is connected to an electric connection pin 58 guided in an insulating manner in the socket 52.

Alternatively, the arrangement according to FIG. 5 can also be realized without the monitor diode 40. In this case, said electric contact site 48 and said bond wire 44 with said pin 54 insulated within said socket would be omitted.

Figure 6:
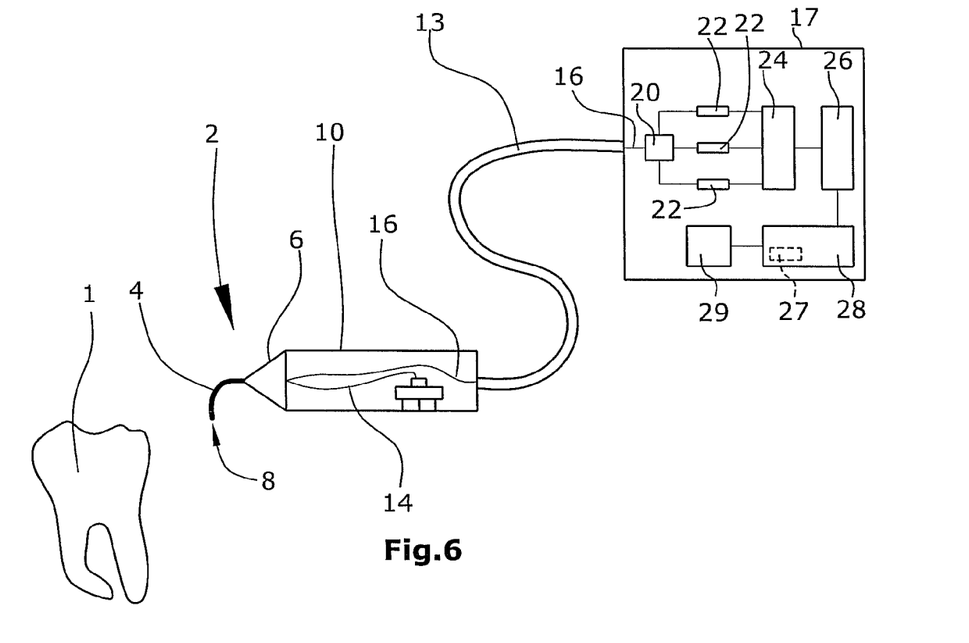
FIG. 6 is a schematic block diagram wherein the light source is arranged in the handle portion.

To keep the radiation losses of the excitation radiation low, one embodiment, shown in FIG. 6, which is similar to the embodiment of FIG. 1, provides that the light source is arranged within handle portion 10. This has the advantage that the emission fibers 14 can be realized with a very short length. The emission fibers 14 and the detection fibers 16 are joined at the distal end of handle portion 10. Following at the distal end is an inspection probe with shaft and coupling member, with the emission fibers 14 and the detection fibers 16 being guided therein. Distally, the emission and detection fibers terminate together with the distal end of the shaft. The fluorescent radiation excited on the tooth 1 will be transmitted from tooth 1 via the detection fibers 16 to a receiving unit 20 located within device 17. The detection fibers 16 are guided, from the proximal handle portion 10 to the receiving unit 20, in the light conductor cable 13. In FIG. 6, there is used the light source from FIG. 5.

Figure 7:
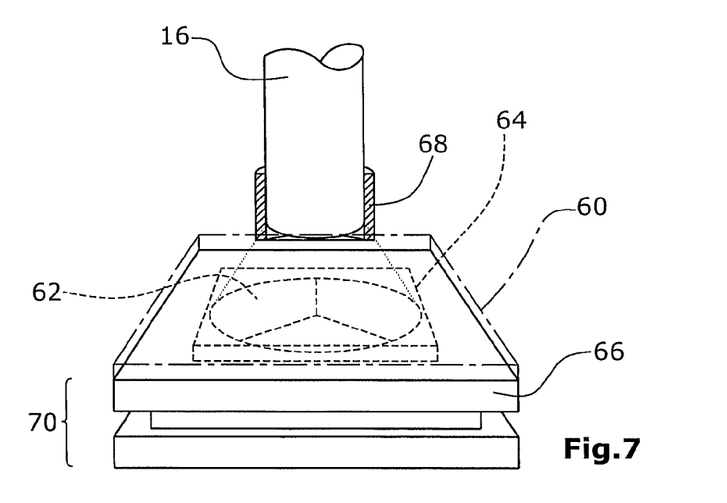
FIG. 7 is a view of a device with a semiconductor sensor arrangement.

FIG. 7 shows a bundle of detection fibers 16 which, via a semiconductor sensor arrangement 62 according to the invention and at a defined distance from the surface of the semiconductor sensor arrangement 62, are centrically positioned with the aid of a light conductor support 68. Said light conductor support 68 is fastened, although not shown here, to the casing of the semiconductor sensor arrangement 62. The semiconductor sensor arrangement 62 comprises three sensors, arranged within a circle, by which the fluorescent radiation excited on the tooth via the emission fibers 14 will be captured in three mutually separated wavelength ranges and will be converted into three electric signals. Said three sensors are sensors for the basic colors red, green and blue. Each of said basic colors has a circular segment of 120° assigned thereto. The distance between the end face of the detection fibers 16 and the surface of the semiconductor sensor arrangement 62 will safeguard a complete illumination of the three sensors. When using wide-angle light conductors, the distance between the end face of the detection fibers 16 and the surface of the semiconductor sensor arrangement 62 can be less than 2 mm. Between the detection fibers 16 and the semiconductor sensor arrangement 62, a prefilter 64 for suppressing the excitation radiation can be arranged. Said prefilter 64 is fixed on the semiconductor sensor arrangement 62 with the aid of an optically transparent casting compound.

Figure 8:
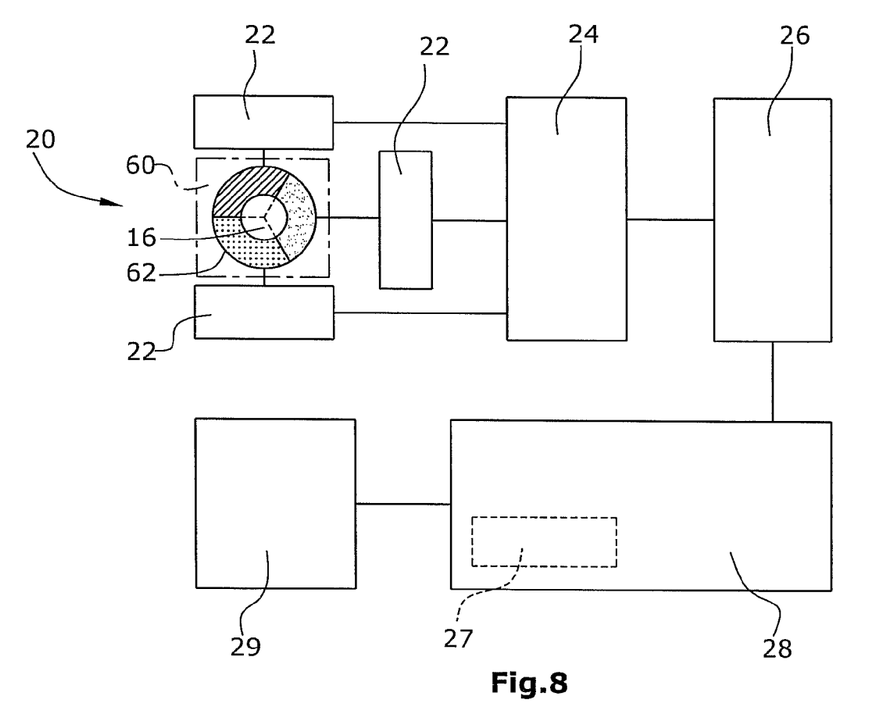
FIG. 8 is a block diagram of the device with receiving unit, amplifier, subtractor, evaluation unit and display unit.

FIG. 8 shows a block diagram of the device of the invention. The detection fibers 16 for conducting the radiation returned by the tooth are centrally positioned above a semiconductor sensor arrangement 62 at a defined distance from the semiconductor sensor arrangement 62. The semiconductor sensor arrangement 62 comprises three sensors arranged within a circle and operative to capture, in three mutually separated wavelength ranges, the fluorescent radiation excited on the tooth or in the gingival pocket via the emission fibers 14 and to convert this radiation into three electric signals. As depicted in FIG. 1, these signals will be supplied via separate preamplifiers 22, a lock-in amplifier 24 and a subtractor 26 to an evaluation unit 28. There, the measurement values will be compared to comparative measurement values stored in a memory 27, and a value will be output which can be displayed on a display unit 29. If said value is above a certain value, this will indicate that the tooth is bacterially infected.

FIG. 9 shows a block diagram which is very similar the one in FIG. 6, with the difference that the end face of the bundle of emission and detection fibers is coupled to the end face of a light-conducting element 9.

Said light-conducting element 9 is guided within a centering device 15 and projects from the proximal end of said centering device 15 from the latter. The centering device 15 and thus the light-conducting element 9, together with the bundle of emission and detection fibers 14,16, are pressed against each other within a plug and coupling element 11 by means of a spring. Such a plug and coupling element 11 can be a commercially available ST plug provided with a bayonet catch. Said plug and coupling element 11 is arranged internally of handle portion 10. The light-conducting element 9 is pressed back into the first coupling member 7 by the length projecting relative to the proximal end of the centering device 15. Since the light-conducting element 9 is fixed or bonded within the shaft 4 and/or the distal end of coupling member 6, the light-conducting element 9 which in this case is a flexible light-conducting fiber made of plastic, is bent within the coupling member 6. By said bending, the light-conducting element 9 is subjected to tension, with the effect that the light-conducting element 9 is permanently pressed against the bundle of emission and detection fibers 14,16. This will safeguard a good incoupling of the radiation from the bundle of emission and detection fibers 14,16 into the light-conducting element 9, and vice versa.

At the connection site, the excitation radiation from the emission fiber 14 will be coupled into the light-conducting element 9. The light-conducting element 9 is guided within an injection probe 2. Said injection probe 2 comprises a shaft 4 and a coupling member 6. The light-conducting element 9 can terminate at its distal end together with the distal end of said shaft 4 or distally project therefrom, extending from the first shaft 5 maximally by 30 mm. The light distally exiting from the light-conducting element 9 will illuminate the tooth portion under examination. The light returned by the tooth portion under examination will be received by the distal end of the light-conducting element 9 and be guided to a receiving unit 20 via the detection fibers 16.

Alternatively, the light-conducting element 9 can also be made of sapphire or other mineral materials. The connection between the light-conducting element 9 and the bundle of emission and detection fibers 14,16 can also be realized without bending the light-conducting element 9, especially if the light-conducting element 9 is rigid. The light-conducting element 9 and the bundle of emission and detection fibers 14,16 can have a spherical end face so as to achieve a better incoupling of the light.

Further, the light-conducting elements 9 can consist of a plurality of light conductors, i.e. the light-conducting element 9 consists of light conductor bundle. These light conductors have each have a diameter of about 30 μm. Also these light conductors can be made of sapphire or other mineral materials or plastics.

Further, in addition to the fluorescence signals of the illuminated tooth portions, also the fluorescence signals of the light-conducting element 9 can received by the receiving unit 20. Also these latter fluorescence signals will then be converted into electric signals. Via separate preamplifiers 22, a lock-in amplifier 24 and a subtractor 26, these signals will be supplied to evaluation unit 28. Within the memory 27 which is located internally of evaluation unit 28, there can additionally be deposited three-dimensional measurement values of the materials of various possible light-conducting elements 9. The measured fluorescence signals of the light-conducting element 9 can be compared to the stored measurement values. In this manner, it can be detected of which material the light-conducting element 9 is made. The sensitivity of the measurement can be adapted to the material of the light-conducting element.

The invention claimed is:

1. A device for detecting signs of bacterial infection of teeth, comprising:
   a light source,
   a receiving unit,
   an evaluation unit coupled to the receiving unit,
   at least one emission fiber coupled to the light source, and
   at least one detection fiber coupled to the receiving unit,
   wherein
   the acceptance angle of both the emission and detection fibers is larger than 45°.

2. The device of claim 1, wherein the numerical aperture of the light source is larger than or equal to the numerical aperture of the at least one emission fiber.

3. The device of claim 1, wherein the light source is a LED chip.

4. The device of claim 3, wherein a distance of less than 0.3 mm, preferably 0 mm, exists between the LED chip and the proximal end face of the at least one emission fiber.

5. The device of claim 3, wherein, between the LED chip and the proximal end face of the at least one emission fiber, a medium is arranged that has a refractive index between that of the emission fiber and that of the surface of the LED chip.

6. The device of claim 3, wherein the proximal end face of the emission fiber adjacent the light-emitting surface of the LED chip is completely covered by the light-emitting surface of the LED chip.

7. The device of claim 3, wherein the LED chip emits light in the UV range in the visible range, preferably violet light in a wavelength range from 390 nm to 420 nm.

8. The device of claim 1, wherein the whole distal end face of a bundle of emission and detection fibers is coupled to the proximal end face of at least one light-conducting element, the light-conducting element conducting the excitation radiation emitted from the light source via the emission fibers to the tooth and the fluorescent radiation coming from the tooth.

9. The device of claim 8, wherein the light-conducting element, formed by a single light conductor or a bundle of light conductors, has an acceptance angle larger than 35°, preferably larger than 40°.

10. The device of claim 8, wherein the light-conducting element is guided within an inspection probe comprising a shaft and a coupling portion.

11. The device of one claim 8, wherein the distal end face of the bundle of emission and detection fibers and the proximal end face of the light-conducting element are pressed against each other by means of a spring force.

12. The device of claim 8, wherein the proximal end face of the light-conducting element and the distal end face of the bundle of emission and detection fibers (each have a spherical surface.

13. The device of claim 1, wherein the emission and detection fibers are guided at the distal end within an inspection probe comprising a shaft and a coupling portion.

14. The device of claim 1, wherein the length of the at least one emission fiber or the total length of the at least one emission fiber and of the at least one light-conducting element is less than 60 cm, preferably less than 10 cm.

15. The device of claim 10, wherein the proximal end of the inspection probe is connectable to a handle portion, the emission a and detection fibers being guided in the handle portion, in that the connection site is located within the handle portion between the bundle of emission and detection fibers and the light-conducting element.

16. The device of claim 15, wherein the light source is arranged within the handle portion.

17. The device of claim 1, wherein the receiving unit comprises a semiconductor sensor arrangement, wherein three sensors are arranged within a surface which sensors detect the fluorescent radiation, excited via the at least one emission fiber on the tooth and returned via the detection fiber, in three mutually separated wavelength ranges, wherein the light cone emitted from the proximal end of the detection fiber illuminates the sensor surface of the semiconductor sensor arrangement without interposition of optical lenses.

18. The device of claim 17, wherein a preferably dielectric optical prefilter for the suppression of the excitation radiation is arranged between the at least one detection fiber and the semiconductor sensor arrangement and is fixed on the semiconductor sensor arrangement by means of an optically transparent casting compound.

19. The device of claim 14, wherein the evaluation unit has stored therein data sets in the form of three-dimensional measurement values, said evaluation unit comparing the measured measurement values with the stored data sets and outputs a result regarding the bacterial infection of a tooth, portion examined.

* * * * *